(12) United States Patent
Barr

(10) Patent No.: US 8,747,311 B2
(45) Date of Patent: Jun. 10, 2014

(54) METHOD AND APPARATUS FOR EVALUATING THE EFFECTS OF INTERNAL AND EXTERNAL STRESS INFLUENCES

(75) Inventor: Lori Lee Barr, Austin, TX (US)

(73) Assignee: Make3Wishes, LLC, Austin, TX (US)

( * ) Notice: Subject to any disclaimer, the term of this patent is extended or adjusted under 35 U.S.C. 154(b) by 438 days.

(21) Appl. No.: 12/949,498

(22) Filed: Nov. 18, 2010

(65) Prior Publication Data

US 2011/0118558 A1     May 19, 2011

Related U.S. Application Data

(60) Provisional application No. 61/262,847, filed on Nov. 19, 2009.

(51) Int. Cl.
| | | |
|---|---|---|
| *A61B 5/00* | (2006.01) | |
| *G09B 3/00* | (2006.01) | |
| *G09B 1/30* | (2006.01) | |
| *G09B 1/18* | (2006.01) | |

(52) U.S. Cl.
CPC .. *G09B 1/30* (2013.01); *G09B 1/18* (2013.01); *G09B 3/00* (2013.01)
USPC .......................................... 600/300; 434/322

(58) Field of Classification Search
CPC . A63F 13/10; A63F 13/00; A63F 2300/5533; A63F 2300/65; A63F 2300/6045; A61B 10/0275; A61B 5/0042; A61B 5/024; A61B 5/0476; A61B 5/055; A61B 5/1121; A61B 5/4585; A61B 5/4815; G06F 3/14; G06F 2203/00; G06F 2203/011; G09B 5/00–5/14; G09B 7/00–7/12; G09B 25/00–25/08; G09B 29/00–29/14; G09B 21/00–21/06
See application file for complete search history.

(56) References Cited

U.S. PATENT DOCUMENTS

| | | | | |
|---|---|---|---|---|
| 1,539,868 | A | * | 6/1925 | Roberts ........................... 40/495 |
| 1,979,593 | A | * | 11/1934 | White ........................ 273/148 R |
| 3,732,632 | A | * | 5/1973 | Dyer ............................. 434/198 |
| 4,021,940 | A | * | 5/1977 | Saint ............................. 434/348 |
| 4,308,678 | A | | 1/1982 | Slobin |
| 5,643,173 | A | | 7/1997 | Welles |
| 6,304,782 | B1 | | 10/2001 | Van Dick |
| 6,641,599 | B2 | | 11/2003 | Peterson |
| 7,273,454 | B2 | * | 9/2007 | Raymond et al. ............. 600/301 |
| 7,507,584 | B2 | | 3/2009 | Asberg |
| 8,100,829 | B2 | * | 1/2012 | Rothman et al. ............. 600/300 |
| 8,262,474 | B2 | * | 9/2012 | McMain ......................... 463/30 |
| 8,677,281 | B2 | * | 3/2014 | Morris .......................... 715/863 |

(Continued)

*Primary Examiner* — Bill Thomson
*Assistant Examiner* — Shirley Jian
(74) *Attorney, Agent, or Firm* — Taylor Russell & Russell, P.C.

(57) ABSTRACT

A measuring device and method is for enabling a user to measure and record changes in emotion during the day and translate it into a relative stress value per day. It may be used to accumulate the positive and negative emotional reactions that a user experiences during a predetermined time period. This method and device will provide a record of the associated distress and eustress and the cumulative effect therefrom on the individual. The user has a visual display of whether or not the emotions felt during a given day are positive or negative. The recognition of the stress level may remind or enable the user to take some action that will counterbalance excessive negative emotions known to contribute to major diseases and engage in activities that reduce or relieve the stress influences on the user before the end of each day.

13 Claims, 3 Drawing Sheets

(56) References Cited

U.S. PATENT DOCUMENTS

| | | | |
|---|---|---|---|
| 2002/0005865 A1* | 1/2002 | Hayes-Roth | 345/706 |
| 2006/0206013 A1* | 9/2006 | Rothman et al. | 600/300 |
| 2007/0100666 A1 | 5/2007 | Stivoric et al. | |
| 2008/0176655 A1* | 7/2008 | James et al. | 463/42 |
| 2008/0195980 A1* | 8/2008 | Morris | 715/864 |
| 2008/0208015 A1* | 8/2008 | Morris et al. | 600/301 |
| 2008/0214903 A1* | 9/2008 | Orbach | 600/301 |
| 2009/0025625 A1 | 1/2009 | Lee | |
| 2009/0082636 A1* | 3/2009 | Vallone | 600/300 |
| 2009/0105550 A1* | 4/2009 | Rothman et al. | 600/300 |
| 2010/0267450 A1* | 10/2010 | McMain | 463/30 |
| 2011/0245708 A1* | 10/2011 | Finkel et al. | 600/544 |
| 2012/0130196 A1* | 5/2012 | Jain et al. | 600/300 |

* cited by examiner

400

40 — DETERMINING A TIME INTERVAL FOR RECORDING EMOTIONAL RESPONSES BY AN INDIVIDUAL TO LIFE EVENTS

42 — JUDGING AND ASSIGNING POSITIVE AND NEGATIVE MEASURES OF EMOTIONAL RESPONSES PERCEIVED BY THE INDIVIDUAL TO EACH INSTANCE OF INTERNAL AND EXTERNAL LIFE EVENTS DURING THE TIME INTERVAL

44 — ACCUMULATING THE MEASURES OF THE EMOTIONAL RESPONSES PERCEIVED BY THE INDIVIDUAL DURING THE DETERMINED TIME PERIOD

46 — EVALUATING THE LEVEL OF DISTRESS AND EUSTRESS ON THE INDIVIDUAL DURING THE TIME INTERVAL BASED ON THE ACCUMULATED MEASURES OF EMOTIONAL RESPONSES PERCEIVED DURING THE TIME INTERVAL BY THE INDIVIDUAL

48 — USING THE LEVEL OF DISTRESS AND EUSTRESS AS A REFERENCE TO CHANGE AND BALANCE EMOTIONAL REACTIONS TO LIFE EVENTS BY THE INDIVIDUAL

FIGURE 3

METHOD AND APPARATUS FOR EVALUATING THE EFFECTS OF INTERNAL AND EXTERNAL STRESS INFLUENCES

This application claims benefit of U.S. Provisional Application No. 61/262,847 filed on Nov. 19, 2009.

FIELD OF THE INVENTION

The subject invention relates generally to the field of health and fitness is intended for use in conjunction with self-monitored wellness and fitness programs. More particularly, a measuring tool is disclosed that allows the user to assess the effects of external and internal stress influences that may impact the user by negating the positive effects of other attempts to improve one's health and/or fitness.

BACKGROUND

There are acute and chronic stressors that appear to have interwoven and cumulative effects on the human body with regard to some disease processes. Both stimuli cause harm when a negative emotional response is elicited. A negative emotional response leads to activation of the sympathetic nervous system and the hypothalamic/pituitary axis. This negative emotional response may be complicated by inadequate health maintenance. Stress is a physiological effect on the body caused by the negative emotional response to either internal or external stimulus. When unchecked physiologic changes occur in the body due to a negative emotional response, the result can contribute to increased risk of physical and psychological disease. For example, stress contributes to the effects of colds, depression, HIV/AIDS, slowed wound healing, infections, rheumatoid arthritis, asthma and cardiovascular disease. Jobs that are perceived by a worker as hectic or highly demanding and that do not allow the worker individual decision making opportunities and personal freedoms are environmental factors that over time lead to job-related stress. The purpose of this invention is to provide a means to recognize, evaluate, and measure underlying emotions that have a negative effect on health.

While there are many different levels of tolerance of stress, it is far more common for people to totally ignore signs of stress within the body, which signify underlying fears, worries and doubts than it is for them to have a high tolerance level for stress. Over time, especially if a person is suppressing knowledge of stress and anxiety within the body, the end result is depression and anger that is turned inward and which may result in disease and disintegration of the body.

Because factors that increase or relieve emotional stress are often ignored or disregarded, there is a need to provide a mechanism to evaluate the stress a particular individual perceives during the day. This invention provides a mechanism for users to be cognizant of the factors that contribute to stress and record the associated changes in their wellbeing due to these stress factors.

SUMMARY OF INVENTION

Individuals are very good at perceiving their emotions and are notoriously bad at determining whether emotions they feel are causing them stress. Stress comes in two forms, distress, the negative form of stress that harms the body, mind and spirit and eustress, the positive form of stress that energizes individuals into vigorous, enjoyable living. Distress is a harmful physiological effect on the body that supports the development of illness caused by a negative emotional response to either an internal or external stimulus. For example, a squirrel darts in front of your car and you almost have a head on collision as you dodge it. You feel scared and your adrenal glands release a large amount of adrenaline into the blood stream that affects a variety of organs. Eustress is a beneficial physiological effect on the body that supports health caused by a positive emotional response to either an internal or external stimulus. For example, the practice or prayer or meditation causes a feeling of peace and lowers the heart rate and blood pressure.

A measuring device and method is provided that will enable a user to measure and record changes in emotion during the day and translate it into a relative distress and eustress value per day. It may be used to accumulate the positive and negative emotional reactions that a user experiences during a predetermined time period. This method and device will provide a record of the associated stress and its cumulative effect.

In one embodiment the device is a comprised of a circular rotating data measuring wheel. The wheel is marked with a cursor line and is rotatably mounted by means of an axle pin onto a backing board or card. The wheel may be provided with a locking mechanism to releasably maintain the current position of the wheel on the backing board or card. The locking mechanism may be a sleeved backing board or card with the wheel rotatably mounted within the sleeve to frictionally restrain the wheel. The axle pin may be provided with flanges or washers to frictionally retain the wheel at a desired position with respect to the cursor line.

The backing board or card is marked with a graduated circle centered about the axle pin. The graduated circle on the backing board is configured into two semicircular separately graduated sections so that the graduations on each semicircular section will correspond with the cursor on the rotating wheel. The graduated circle has a zero position designated as "0" to serve as a marker to indicate a neutral or zero stress situation. The right semicircular section has positive "+" graduations that serve as a means for the user to measure emotional reactions to life events like calm, laughter and ecstasy that an individual user perceives as positive to the user's well-being. The left semicircular section has negative "−" graduations that serve as measure of emotional reactions to life events like pain, sadness or anger that an individual user perceives as negative to the user's well-being.

The device may be used to log or keep a rolling score of the emotions that a user felt that translates into wither distress or eustress during a particular day. To do so, the user first sets the cursor to the zero "0" gradation of the graduated wheel. Then when the user experiences an emotion that user perceives to be increasing or decreasing the user's stress, the user assigns a grade to the emotion he or she feels related to a life event using a predetermined specified scale. For instance, a scale ranging from plus or positive one "+1" to plus or positive ten "+10" may be used to grade an emotion that is perceived by the user to decrease or relieve stress. Similarly, a scale ranging from a minus or negative one "−1" to minus or negative ten "−10" may be used to grade an emotion that serves to increase stress.

When the user has graded and assigned a value to their emotion according to the selected scale, that value can be recorded on the measuring device by increasing or decreasing the cursor position by the positive or negative amount assigned to the emotion from the event to the assigned value on the graduated wheel. As an example of use, the cursor is set at zero "0" on the graduated wheel at the start of the day. When the user experiences a life event causing either notable positively- or negatively-perceived emotion during the day, the user assigns a value to that emotion such as a +8 value for joy at receiving flowers from a beau. Then the user uses the device to record the perceived emotion value of +8 by moving the wheel 8 graduations to align the cursor with the eighth graduation on the positive or "+" side of the wheel. If during the day, a second emotion-provoking event is perceived by the user, the user will assign a value to that emotion on the predetermined scale. If the second event is one that is perceived distressful, such as hitting an animal while driving, the users might assign a −9 value to that increase in negative emotion. At that point the user moves the wheel with respect to the cursor 9 graduations to the left on the negative or "−" side of the wheel, so that the cursor shows a total recorded stress value of −1 for the day.

Similarly, if during the day, a third emotion-provoking event is perceived by the user, the user will assign a value to that event on the predetermined scale. If the user experiences an emotional situation that is perceived by the user as relaxing or supportive of his or her well-being, such as participation in an exercise class, the user might assign a value of +5 for such an emotion. At that point the user will move the wheel right five graduations with respect to the cursor, toward the positive or "+" side of the wheel, so that the cursor will indicate on the graduations on the wheel a total recorded stress value for the day as +4 at the cursor. The sequence is repeated throughout the day by the user as a means to record the user's emotional response to life events. If during the day the recorded graduations on the wheel, or total recorded positive or negative emotions, exceeds the total graduations on the wheel, whether positive or negative, the user may record the total reached, reset the scale at zero, and continue recording as set forth above.

An electronic measuring tool may also be provided with an emotion calculator as a method to evaluate and record the emotional response to individual events perceived by the user and subsequent translation into a relative stress score for the day or other predetermined time interval. Such an electronic measuring tool may be a programmed computer chip or processor to record a total value of perceived daily emotions. Such a electronic measuring tool may be adapted as an application for a personal computer, smart phone or a personal digital assistant (PDA) such as an iPod®, iPhone® or a Blackberry® or other calculator or cell phone device using an electronic version of the measurement algorithm provided above for the mechanical version of the device.

The measuring device and method described herein provides a measuring tool to assist the user in judging and recording the effects of external stimuli and internal feelings on the user's eustress/distress spectrum which then contributes to one's ability to live a life of ease vs. disease. The user has a visual display of whether or not the emotions felt during a given day are positive or negative. The recognition of the stress level may remind or enable the user to take some action that will counterbalance excessive negative emotions known to contribute to major diseases such as heart attack and engage in activities that reduce or relieve the stress influences on the user before the end of each day.

An embodiment of a method for evaluating a cumulative level of distress and eustress on an individual comprises determining a time interval for recording emotional responses by the individual to life events, judging and assigning positive and negative measures of emotional responses perceived by the individual to each instance of internal and external life events during the determined time interval, accumulating the measures of the emotional responses perceived by the individual during the determined time interval, evaluating the level of distress and eustress on the individual during the time interval based on the accumulated measures of emotional responses perceived during the time interval by the individual, and using the level of distress and eustress as a reference to change and balance emotional reactions to life events by the individual. The method may further comprise evaluating long term trends over time of cumulative distress and eustress on the individual by comparing changes in the level of distress and eustress between successive time intervals. The determined time interval may a day. The method may further comprise assigning positive numeric values based on an intensity of the positive measures of emotional responses and assigning negative numeric values based on an intensity of the negative measures of emotional responses. The method may further comprise providing a measuring device having a positive and negative graded scale, setting the measuring device to a value of zero at the beginning of the time interval, entering the assigned positive and negative numeric values based on the intensity of the measures of emotional responses into the measuring device during the time interval, and evaluating the level of distress and eustress on the individual during the time interval based on the final accumulated numeric values in the measuring device of the intensity of the measures of emotional responses perceived during the time interval by the individual. The measuring device may be selected from the group consisting of a circular rotating data measuring wheel, an electronic measuring device, a personal digital assistant, a measurement application for a computer, and a measurement application for a cell phone.

Another embodiment is a device for evaluating a cumulative level of distress and eustress on an individual that comprises a predetermined time interval for recording emotional responses by the individual to life events, positive and negative measures of emotional responses perceived by the individual to each instance of internal and external life events during the predetermined time interval, means for accumulating the measures of the emotional responses perceived by the individual during the predetermined time interval, means for evaluating the level of distress and eustress on the individual during the predetermined time interval based on the accumulated measures of emotional responses perceived during the predetermined time interval by the individual, and the level of distress and eustress being used as a reference to change and balance emotional reactions to life events by the individual. The device may further comprise means for evaluating long term trends over time of cumulative distress and eustress on the individual by comparing changes in the level of distress and eustress between successive time intervals. The device may further comprise means for assigning positive numeric values based on an intensity of the positive measures of emotional responses and assigning negative numeric values based on an intensity of the negative measures of emotional responses. The device may further comprise a measuring device having a positive and negative graded scale, means for setting the measuring device to a value of zero at the beginning of the time interval, means for entering the assigned positive and negative numeric values based on the intensity of the measures of emotional responses into the measuring device during the time interval and means for evaluating the level of distress and eustress on the individual during the time interval based on the final accumulated numeric values in the measuring device of the intensity of the measures of emotional responses perceived during the time interval by the individual. The measuring device may be selected from the group consisting of a circular rotating data measuring wheel, an electronic measuring device, a personal digital assistant, a measurement application for a computer, and a measurement application for a cell phone.

Another embodiment of a method for evaluating a cumulative level of distress and eustress on an individual comprises providing a measuring device having a negative and positive graded scale, the scale being moveable with respect to a cursor on the device, setting the cursor to zero on the measuring scale, providing a relative scale to evaluate and value emotional responses to individual life events and to translate this evaluation into a numeric distress indicator value, assigning a perceived numeric value relative to the intensity of the positive and negative emotion felt by the user of the device who perceives the life event as being emotional, moving the cursor on the graded scale of the device by an amount equal to the assigned positive and negative numeric value of each perceived emotional event, evaluating subsequent emotional events in the same way, and adding and subtracting the assigned relative emotional value to the on-going tally of emotional values, and determining the cumulative daily value of the eustress and distress based on the final daily reading of the indicator and using it as a reference to change and balance emotional reactions to life events by the individual. The measuring device may be selected from the group consisting of a circular rotating data measuring wheel, an electronic measuring device, a personal digital assistant, an application for a personal computer, and a measurement application for a cell phone.

Yet another embodiment of a device for evaluating a cumulative level of distress and eustress on an individual comprises a circular wheel marked with a cursor line that is mounted on a graduated backing board, the wheel is mounted for rotation on the graduated backing board about an axis pin, the axis pin is configured to frictionally restrain the wheel from random rotation about the axis pin by the use of flanges and washers to allow a user to rotate the wheel a desired amount about the pin in relation to the cursor line, the backing board is marked with two semicircle graduated sections that correspond with the outer edge of the rotating wheel, a negative semicircle section being to a user's left and a positive semicircular section being to a user's right, each semicircular section is marked with a desired number of equal graduations to provide a recording scale that extends around its outer edge for recording numeric values of emotional distress and eustress responses to individual life events, the negative semicircular section is provided with graduations indicating a negative scale from 0 to 180, and the positive section is provided with graduations indicating a positive scale from 0 to 180 and the evaluation of cumulative levels of distress and eustress being used as a reference to change and balance emotional reactions to life events by the individual. The backing board may be a backing card. The wheel may be rotatably mounted onto a sleeved, windowed envelope to frictionally restrain the wheel at a desired location with respect to a cursor line on the sleeved envelope. The wheel may be rotatably mounted within a sleeved, windowed envelope. A positive scale from +1 to +10 may grade a positive emotion that translates to eustress and a negative scale of from −1 to −10 grades a negative emotion that translates to distress. A value of emotion may be recorded on the device by moving the wheel housing cursor line to the assigned value of the perceived emotion on the backing board. The wheel may be marked with semicircular graduations for measuring a value of an emotional response and the backing card may be marked with an indicator line in place of the cursor, to serve as a reference for relative movement of the graduated wheel.

BRIEF DESCRIPTION OF THE DRAWINGS

FIG. 3 is a flow chart showing an embodiment of a method for evaluating a cumulative level of distress and eustress on an individual; and

DETAILED DESCRIPTION OF EMBODIMENTS

Figure 1:
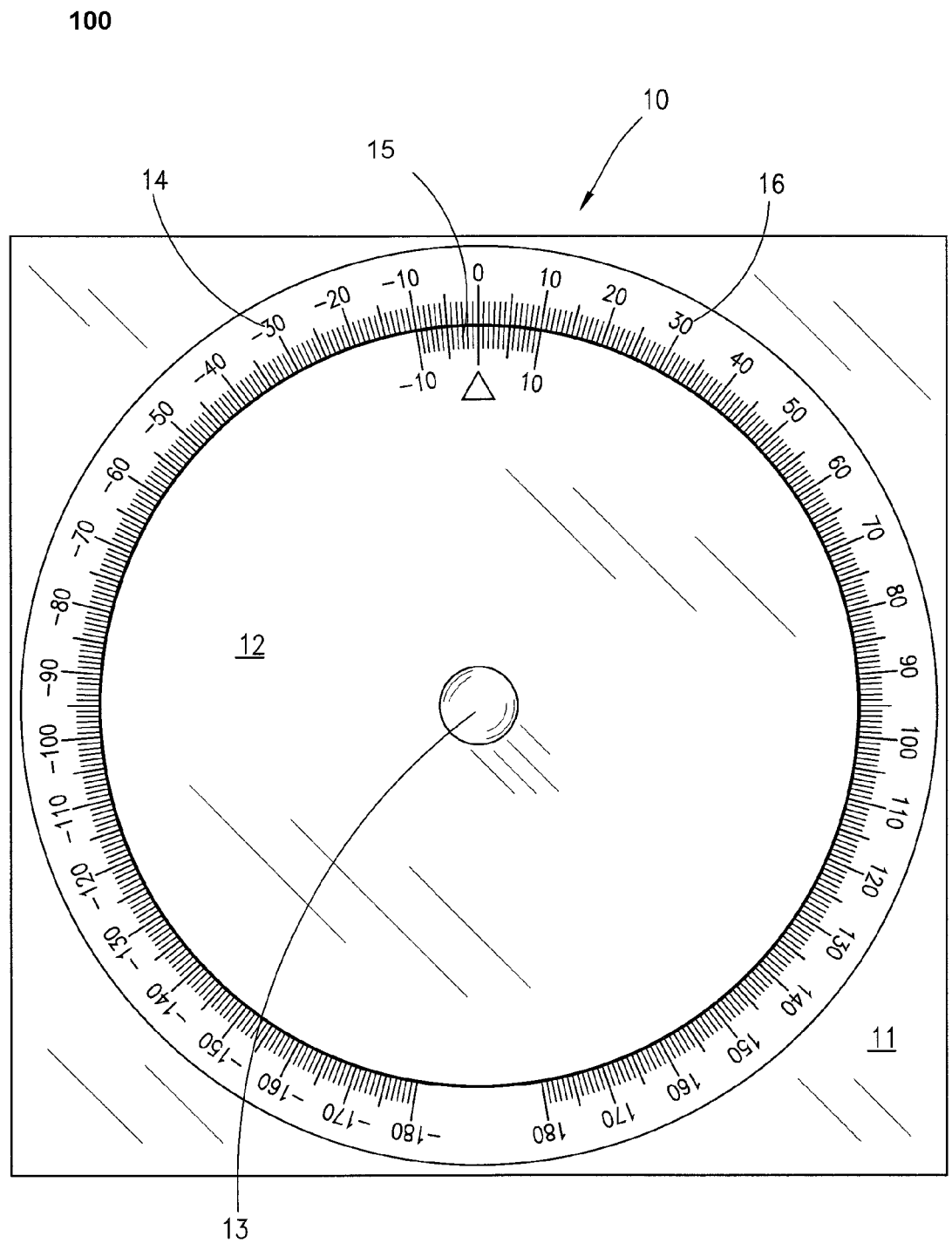
FIG. 1 is an illustrative front view of the emotion measuring device described herein.

FIG. 1 shows an illustrative front view of an embodiment of the emotion measuring device described herein. As shown the device 10 is comprised of a circular wheel 12 marked with a cursor line 15 that is mounted on a graduated backing board or card 11. The wheel 12 is mounted for rotation on the graduated backing board or card 11 about an axis pin 13. The axis pin 13 may be configured to frictionally restrain the wheel 12 from random rotation about the axis pin 13 by the use of flanges or washers so as to allow a user to rotate the wheel 12 a desired amount about the pin 13 in relation to the cursor line 15. The wheel 12 may also be rotatably mounted onto or within a sleeved, windowed, envelope, not shown, to fractionally restrain the wheel at a desired location with respect a cursor line on the sleeved envelope.

The backing board or card 11 is marked with two semicircular graduated sections that correspond with the outer edge of the rotating wheel 12, a negative semicircular section 14 to the user's left and a positive semicircular section 16 to the user's right. Each semicircular section 14 and 16 is marked with a desired number of equal graduations to provide a recording scale that extends around its outer edge. As shown, negative section 14 is provided with graduations indicating a negative or minus "−" scale from 0 to 180. The positive section 16 is provided with graduations indicating a positive or plus "+" scale from 0 to 180.

Figure 2:
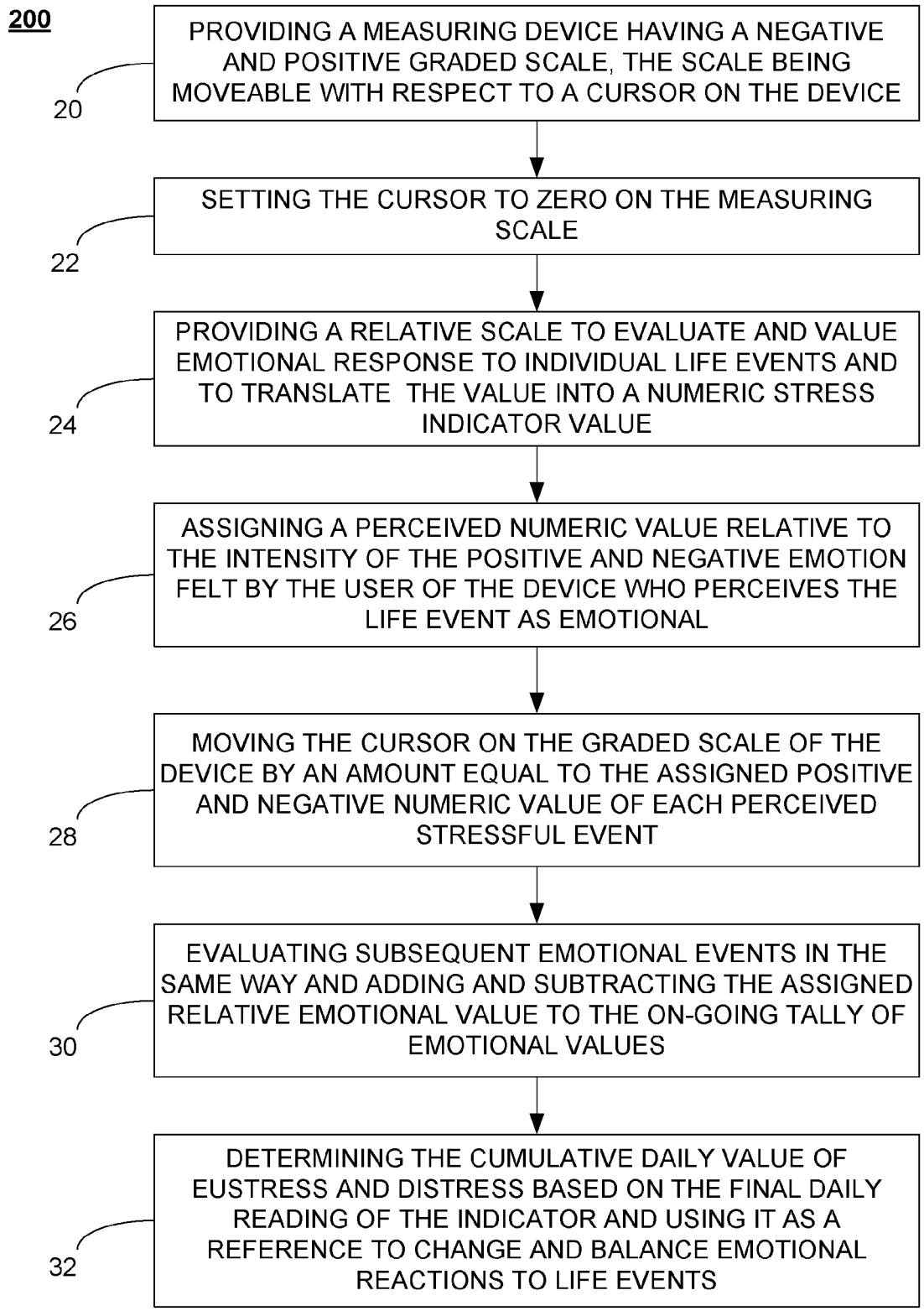
FIG. 2 is a flow chart showing an embodiment of a method for recording an emotional stress level utilizing the device shown in FIG. 1.

FIG. 2 is a flow chart 200 showing an embodiment of a method for recording an emotional stress level utilizing the device shown in FIG. 1. As shown in FIG. 2, the measuring device (10 in FIG. 1) is used to log or keep track of the influences that a user may perceive as increasing or decreasing stress during a particular day 20. To begin use of the device (10 in FIG. 1), a user will each day first set or align the cursor line (15 in FIG. 1) with the zero "0" gradation 22 on the backing card (11 in FIG. 1). Then during the day, when the user perceives an emotion strong enough to prompt him or her to grade it, the user will grade the emotion using a specified scale 24.

It is suggested that that the user adopt a positive or plus scale from +1 to +10 to grade a positive emotion that translates to eustress or the "good" stress that propels and energizes and a minus or negative scale from −1 to −10 scale to grade a negatively-perceived emotion that causes distress. The user is encouraged not to limit a grade to +10 or −10 if a particular event might warrant a higher or lower value as perceived by the user.

The following scale serves as guide for the user to measure emotions though users may establish any scale that heightens their awareness of positive and negative stressors.

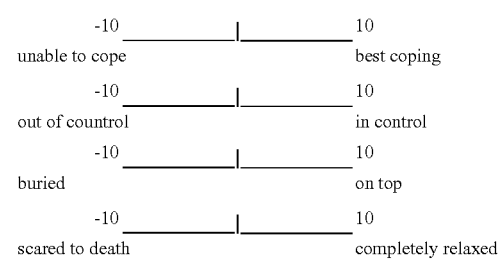

When the user has graded and assigned a relative value to the emotion 26, that value is recorded on the measuring device (10 in FIG. 1) by moving the wheel (12 in FIG. 1) housing the cursor line to the assigned value of the perceived emotion 28 on the backing card (11 in FIG. 1). For example, at the start of a day the cursor is aligned or set at zero "0" on the backing card (11 in FIG. 1). When the user experiences a life event that is triggers a positive emotion such as relaxation, the user may assign a value of +8 to that emotion. The user will then move the cursor (15 in FIG. 1) on the wheel (12 in FIG. 1) eight graduations on the positive or "+" semicircular section (16 in FIG. 1) of the backing card (11 in FIG. 1) so that the cursor line (15 in FIG. 1) is aligned with graduation 8 on the semicircular side (16 in FIG. 1) of the backing card (11 in FIG. 1).

If during the day, a second life event is perceived by the user as a trigger of a recordable emotion, the user will assign a value to that stress on the predetermined scale. For example, the user may assign a value of −9 to a negative emotion, indicating an emotion that caused distress. At that point the user will use the device (10 in FIG. 1) to record the cumulative effect of that stressful event by moving the cursor (15 in FIG. 1) on the wheel (12 in FIG. 1) nine graduations to the left on the negative or "−" semicircular section (14 in FIG. 1) of the backing card (11 in FIG. 1) so that the cursor line (15 in FIG. 1) is now aligned with graduation mark −1 on the negative semicircular section (14 in FIG. 1) of the backing card (11 in FIG. 1). When the event is recorded in this fashion, the cursor line (15 in FIG. 1) will show a total recorded stress value of −1 for the day.

If during the day, a third life event is perceived by the user as emotional, the user will assign a value to that stress on the predetermined scale. If the emotion is one perceived by the user as positive or relaxing, the user may rate that third event as having a stress value of +5. At that point the user will move the cursor (15 in FIG. 1) on the wheel (12 in FIG. 1) five graduations to the right on section (16 in FIG. 1) of the backing card (11 in FIG. 1) so that the cursor line (15 in FIG. 1) of the device (10 in FIG. 1) will then show a total recorded stress value of +4 for the day.

This sequence is repeated by the user to evaluate and record each successive emotional life event during the day that serves to increase either distress or eustress 30. If during the day the score exceeds the total graduations on the scale, whether positive or negative, the user will write down or otherwise record the total reached. Then the cursor (15 in FIG. 1) on the wheel (12 in FIG. 1) can be reset or aligned with "0" on the backing card (11 in FIG. 1) and the user can continue evaluating and recording the user's emotional response to life events as set forth above. At the end of the day the relative stress value, shown on the backing card (11 in FIG. 1) at cursor line (15 in FIG. 1) will be added to the written down or otherwise recorded stress values to provide a total eustress or distress grade for the user during the day.

As an alternate embodiment of the device (10 in FIG. 1), the wheel (12 in FIG. 1) may be marked with semicircular graduations for measuring the value of an emotional response and the backing card (11 in FIG. 1) may be marked with an indicator line, in place of the cursor (15 in FIG. 1), to serve as a reference for relative movement of the graduated wheel (12 in FIG. 1). When the device (10 in FIG. 1) is so configured, the method set forth in FIG. 2 and described herein may be utilized in the same manner to provide a total eustress or distress grade for the user during the day 32.

FIG. 3 is a flow chart 400 showing an embodiment of a method for evaluating a cumulative level of distress and eustress on an individual. The embodiment includes the steps of determining a time interval for recording emotional responses by the individual to life events 40, judging and assigning positive and negative measures of emotional responses perceived by the individual to each instance of internal and external life events during the determined time interval 42, accumulating the measures of the emotional responses perceived by the individual during the determined time interval 44, evaluating the level of distress and eustress on the individual during the time interval based on the accumulated measures of emotional responses perceived during the time interval by the individual 46 and using the level of distress and eustress as a reference to change and balance emotional reactions to life events by the individual 48.

It is thought that measuring device and method described herein and many of its attendant advantages will be understood from the foregoing description. It is also thought that it will be apparent that various changes may be made in the form, construction and arrangement of the components of the measuring device and method such as a dial or meter format for electronic versions of the device without departing from the spirit and scope of the invention or sacrificing all of its material advantages.

The invention claimed is:

1. A computer-implemented method for evaluating a cumulative level of distress and eustress on an individual, the method implemented on a measuring device by software instructions contained in a memory coupled to a computer processor and including a user interface having a display means and an input means, comprising:

providing a negative and a positive graded scale on the measuring device, the scale being moveable with respect to a cursor displayed on the measuring device;

determining a time interval for recording emotional responses by the individual to life events and entering the time interval into the measuring device by the input means;

judging and assigning positive and negative numeric measures of emotional responses perceived by the individual to each instance of life events during the determined time interval and entering the positive and negative numeric measures into the measuring device by the input means;

accumulating the numeric measures of the emotional responses perceived by the individual during the determined time interval by the measuring device;

displaying and evaluating the level of distress and eustress on the individual during the determined time interval based on the accumulated numeric measures of emotional responses perceived during the determined time interval by the individual; and using the displayed level of distress and eustress as a reference to change and balance emotional reactions to life events by the individual.

2. The method of claim 1, further comprising evaluating long term trends over time of cumulative distress and eustress on the individual by comparing changes in the level of distress and eustress between successive time intervals.

3. The method of claim 1, wherein the determined time interval is selected from the group consisting of a day, a week and a month.

4. The method of claim 1, further comprising assigning positive numeric values based on an intensity of the positive measures of emotional responses and assigning negative numeric values based on an intensity of the negative measures of emotional responses.

5. The method of claim 4, further comprising:

providing the measuring device with a displaying the positive and negative graded scale;

setting the measuring device to a value of zero at the beginning of the time interval;

using the input means, entering the assigned positive and negative numeric values based on the intensity of the measures of emotional responses into the measuring device during the time interval; and evaluating the level of distress and eustress on the individual during the time interval based on the final summed numeric values in the measuring device of the intensity of the measures of emotional responses perceived during the time interval by the individual.

6. The method of claim 5, wherein the measuring device is selected from the group consisting of an electronic measuring device, a personal digital assistant, a computer having non-transitory computer readable medium comprising a measurement application, and a cell phone having non-transitory computer readable medium comprising a measurement application.

7. An electronic device having a processor, a user interface including a display means and an input means, and a memory containing software instructions coupled to the processor for evaluating a cumulative level of distress and eustress on an individual, comprising:

the input means for entering into the device a predetermined time interval for recording emotional responses by the individual to life events;

the input means for entering into the device positive and negative numeric measures of emotional responses perceived by the individual to each instance of life events during the predetermined time interval;

the processor for summing the numeric measures of the emotional responses perceived by the individual during the predetermined time interval;

the display means for evaluating the level of distress and eustress on the individual during the predetermined time interval based on the summed numeric measures of emotional responses perceived during the predetermined time interval by the individual; and the display means indicating the level of distress and eustress being used as a reference to change and balance emotional reactions to life events by the individual.

8. The device of claim 7, further comprising means for evaluating long term trends over time of cumulative distress and eustress on the individual by comparing changes in the level of distress and eustress between successive time intervals.

9. The device of claim 7, further comprising means for assigning positive numeric values based on an intensity of the positive measures of emotional responses and assigning negative numeric values based on an intensity of the negative measures of emotional responses.

10. The device of claim 9, further comprising:

the device having the display means for displaying a positive and negative graded scale;

the input means for setting the device to a value of zero at the beginning of the time interval;

the input means for entering the assigned positive and negative numeric values based on the intensity of the measures of emotional responses into the device during the time interval; and the display means for evaluating the level of distress and eustress on the individual during the time interval based on the final accumulated numeric values in the device of the intensity of the measures of emotional responses perceived during the time interval by the individual.

11. The method of claim 10, wherein the device is selected from the group consisting of an electronic measuring device, a personal digital assistant, a computer having non-transitory computer readable medium comprising a measurement application, and a cell phone having non-transitory computer readable medium comprising a measurement application.

12. A method for evaluating a cumulative level of distress and eustress on an individual, comprising:

providing a measuring device having a negative and positive graded scale, the scale being moveable with respect to a cursor on the device;

setting the cursor to zero on the measuring scale;

providing a relative scale to evaluate and value emotional responses to individual life events and to translate this evaluation into a numeric distress indicator value;

assigning a perceived numeric value relative to the intensity of the positive and negative emotion felt by the user of the device who perceives the life event as being emotional;

moving the cursor on the graded scale of the device by an amount equal to the assigned positive and negative numeric value of each perceived emotional event;

evaluating subsequent emotional events in the same way, and adding and subtracting the assigned relative emotional value to the on-going tally of emotional values; and determining the cumulative daily value of the eustress and distress based on the final daily reading of the indicator and using it as a reference to change and balance emotional reactions to life events by the individual.

13. The method of claim 12, wherein the measuring device is selected from the group consisting of a circular rotating data measuring wheel, an electronic measuring device, a personal digital assistant, an application for a personal computer, and a measurement application for a cell phone.

* * * * *